United States Patent [19]

Wolf et al.

[11] Patent Number: 5,718,887
[45] Date of Patent: Feb. 17, 1998

[54] DEODORIZING ACTIVE COMPOUND COMBINATIONS BASED ON α,Ω-ALKANEDICARBOXYLIC ACIDS AND MONOCARBOXYLIC ACID ESTERS OF OLIGOGLYCEROLS

[75] Inventors: Florian Wolf; Manfred Klier; Bernd Traupe, all of Hamburg, Germany

[73] Assignee: Beiersdorf Aktiengesellschaft, Hamburg, Germany

[21] Appl. No.: 497,118

[22] Filed: Jun. 30, 1995

[30] Foreign Application Priority Data

Jul. 4, 1994 [DE] Germany .................... 44 23 410.4

[51] Int. Cl.[6] ................ A61K 7/32; A61K 31/19
[52] U.S. Cl. ............ 424/65; 424/400; 424/401; 514/553
[58] Field of Search ................ 424/5, 400, 401; 514/553

[56] References Cited

U.S. PATENT DOCUMENTS 4,089,942   5/1978   Bore et al. ...................... 424/47

FOREIGN PATENT DOCUMENTS 0 036 134 A2   9/1981   European Pat. Off. .
27 03 642      8/1977   Germany .

*Primary Examiner*—Shelley A. Dodson
*Attorney, Agent, or Firm*—Sprung Kramer Schaefer & Briscoe

[57] ABSTRACT

Cosmetic deodorants comprising mixtures of

I) one or more α,Ω-alkanedicarboxylic acids and
II) one or more monocarboxylic acid esters of di- and/or triglycerol.

14 Claims, No Drawings

DEODORIZING ACTIVE COMPOUND COMBINATIONS BASED ON α,Ω-ALKANEDICARBOXYLIC ACIDS AND MONOCARBOXYLIC ACID ESTERS OF OLIGOGLYCEROLS

The present invention relates to cosmetic active compound combinations, in particular active compound combinations as the active principle in cosmetic deodorants.

Cosmetic deodorants serve to eliminate body odour which is formed when fresh perspiration, which is in itself odourless, is decomposed by microorganisms. The customary cosmetic deodorants are based on various active principles.

In so-called antiperspirants, the formation of perspiration can be suppressed by astringents—chiefly aluminium salts, such as aluminium hydroxychloride (aluminium chlorohydrate). Apart from denaturing the skin proteins, however, the substances used for this purpose intervene drastically in the thermal balance of the axillary region, depending on their dosage, and should at most be used in exceptional cases.

The bacterial flora on the skin can be reduced by the use of antimicrobial substances in cosmetic deodorants. In the ideal case, only the microorganisms which cause odour should be reduced effectively here. In practice, however, it has been found that the entire microflora of the skin may be impaired.

The flow of perspiration itself is not thereby influenced, and in the ideal case only the microbial decomposition of the perspiration is stopped temporarily.

Combination of astringents with antimicrobially active substances in one and the same composition is also customary. However, the disadvantages of the two classes of active compounds cannot be eliminated completely by this route.

Finally, body odour can also be masked by fragrances, a method which meets the aesthetic requirements of the consumer the least, since the mixture of body odour and perfume fragrance smells rather unpleasant.

Nevertheless, most cosmetic deodorants, like most cosmetics overall, are perfumed, even if they comprise deodorizing active compounds. Perfuming can also serve to increase the consumer acceptance of a cosmetic product or to give a product a certain flair.

Needless to say, perfuming of cosmetic formulations containing active compounds, in particular cosmetic deodorants, is frequently problematic, because active compounds and perfume constituents can occasionally react with one another and render each other inactive.

Deodorants should meet the following conditions:

1) They should cause reliable deodorization.
2) The natural biological processes of the skin should not be impaired by the deodorants.
3) The deodorants must be harmless in the event of an overdose or if otherwise not used as specified.
4) They should not become concentrated on the skin after repeated use.
5) They should be easy to incorporate into customary cosmetic formulations.

Both liquid deodorants, for example aerosol sprays, roll-ons and the like, and solid formulations, for example deodorant sticks, powders, powder sprays, intimate cleansing agents and the like, are known and customary.

The object of the present invention was thus to develop cosmetic deodorants which do not have the disadvantages of the prior art. In particular, the deodorants should largely preserve the microflora of the skin, but selectively reduce the number of microorganisms which are responsible for body odour.

It was furthermore an object of the invention to develop cosmetic deodorants which are distinguished by a good skin tolerability. Under no circumstances should the deodorizing active principles become concentrated on the skin.

Another object was to develop cosmetic deodorants which harmonize with the greatest possible diversity of customary cosmetic auxiliaries and additives, in particular with the perfume constituents which are particularly important in formulations having a deodorizing or antiperspirant action.

It was yet another object of the invention to provide cosmetic deodorants which are active over a relatively long period of time, and in particular of the order of at least half a day, without their action noticeably subsiding.

Finally, an object of the present invention was to develop deodorizing cosmetic principles which can be incorporated as universally as possible into the most diverse presentation forms of cosmetic deodorants without being limited to one or a few specific presentation forms.

It has been found, surprisingly, and therein lies the achievement of all these objects, that cosmetic deodorants comprising mixtures of I) one or more α,Ω-alkanedicarboxylic acids and II) one or more monocarboxylic acid esters of di- and/or triglycerol remedy the disadvantages of the prior art.

It is indeed known that fatty acid esters of glycerol (that is to say of monoglycerol) lead to a certain antimicrobial action. It is furthermore known to employ monoglycerol fatty acid esters, in particular glycerol monolaurate, in deodorizing cosmetics. Nevertheless, the action of these monoglycerol esters is far inferior to that of the monocarboxylic acid esters according to the invention.

European Patent Application EP-0 036 134 furthermore describes deodorizing compositions, characterized by a content of derivatives of medium- to long-chain alkanoic acids, which also include the α,Ω-alkanedicarboxylic acids of the general formula

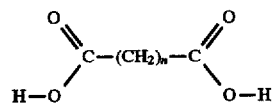

where n=4 to 10, but this specification contains no indication of the teaching presented here.

German Offenlegungsschrift DE-OS 27 03 642 furthermore describes deodorizing compositions for body hygiene which includes, inter alia, certain α,Ω-alkanedicarboxylic acids, but this specification also contains no reference to the teaching presented here.

In particular, no indication that the mixtures according to the invention are distinguished by a super-additive, that is to say synergistic action could be detected from the prior art.

According to the invention, the di- and triglycerol units of the monocarboxylic acid esters according to the invention are in the form of linear, unbranched molecules, that is to say "monoglycerol molecules" etherified via the particular OH groups in the 1- and 3-position.

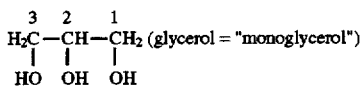

A small content of cyclic di- and triglycerol units and glycerol molecules etherified via the OH groups in the 2-position can be tolerated. However, it is advantageous to keep such impurities as low as is possible.

The diglycerol monocarboxylic acid esters according to the invention are preferably monocarboxylic acid monoesters and are preferably characterized by the following structure (substitution positions shown):

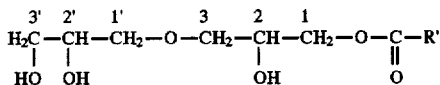

where R' is a hydrocarbon radical,. advantageously a branched or unbranched alkyl or alkenyl radical having 5 to 17 C atoms.

The triglyercol monocarboxylic acid esters according to the invention are preferably monocarboxylic acid monoesters and are preferably characterized by the following structure (substitution positions shown):

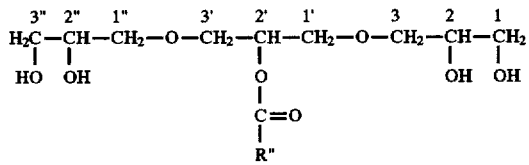

where R" is a hydrocarbon radical, advantageously a branched or unbranched alkyl or alkenyl radical having 5 to 17 C atoms.

The acids on which these esters are based are
hexanoic acid (caproic acid) (R' and R"=—$C_5H_{11}$),
heptanoic acid (oenanthic acid) (R' and R"=—$C_6H_{13}$),
octanoic acid (caprylic acid) (R' and R"=—$C_7H_{15}$),
nonanoic acid (pelargonic acid) (R' and R"=—$C_8H_{17}$),
decanoic acid (capric acid) (R' and R"=—$C_9H_{19}$),
undecanoic acid (R' and R"=—$C_{10}H_{21}$),
10 -undecenoic acid (undecylenic acid) (R' and R"=—$C_{10}H_{19}$),
dodecanoic acid (lauric acid) (R' and R"=—$C_{11}H_{23}$),
tridecanoic acid (R' and R"=—$C_{12}H_{25}$),
tetradecanoic acid (myristic acid) (R' and R"=—$C_{13}H_{27}$),
pentadecanoic acid (R' and R"=—$C_{14}H_{29}$),
hexadecanoic acid (palmitic acid) (R' and R"=—$C_{15}H_{31}$),
heptadecanoic acid (margaric acid) (R' and R"=—$C_{16}H_{33}$),
octadecanoic acid (stearic acid) (R' and R"=—$C_{17}H_{35}$).

R' and R" are particularly favourably chosen from the group consisting of unbranched alkyl radicals having odd C numbers, in particular having 9, 11 and 13 C atoms.

The esters of diglycerol are in general preferable to those of triglycerol.

Especially favourable esters are
diglycerol monocaprate (DMC) R'=9
triglycerol monolaurate (TML) R"=11
diglycerol monolaurate (DML) R'=11
triglycerol monomyristate (TMM) R"=13.

Diglycerol monocaprate (DMC) has proved to be the preferred monocarboxylic acid ester according to the invention.

The diglycerol mono-fatty acid esters according to the invention are preferably esterified in the 1-position and the triglycerol mono-fatty acid esters according to the invention are preferably esterified in the 2'-position.

According to an advantageous embodiment of the present invention, an additional content of di- or triglycerol esterified in another position is used, as is, where appropriate, a content of the different diesters of di- or triglycerol.

Those monocarboxylic acid esters which are obtainable by a process as described in DE-A 38 18 293 are particularly advantageous.

The diglycerol esters, which are distinguished by two centres of asymmetry, and the triglycerol esters, which are distinguished by three centres of asymmetry, are active according to the invention in all their configurations. The diglycerol esters have four stereoisomers and the triglycerol esters have eight stereoisomers.

In the diglycerol esters, the 2- and the 2'-position are centres of asymmetry. The 2S2'S, the 2R2'S, the 2S2'R and the 2R2'R configuration are active and equally of advantage according to the invention.

In the triglycerol esters, the 2-, the 2'- and the 2"-position are centres of asymmetry. The 2S2'S2"S, the 2R2'S2"S, the 2S2'R2"S, the 2R2'R2"S, the 2S2'S2"R, the 2R2'S2"R, the 2S2'R2"R and the 2R2'R2"R configuaration are active and equally of advantage according to the invention.

It has proved to be favourable to use racemic mixtures of the stereoisomers.

According to an advantageous embodiment of the present invention, mixtures of one or more monocarboxylic acid esters of diglycerol with one or more monocarboxylic acid esters of triglycerol are used.

According to another advantageous embodiment of the present invention, one or more monocarboxylic acid esters of diglycerol and/or one or more monocarboxylic acid esters of triglycerol are employed in combination with other active compounds (substitute active compounds), auxiliaries, extenders and/or additives customary in cosmetics.

The extenders and/or substitute active compounds are then advantageously present in a concentration of up to 50 parts by weight, preferably up to 35 parts by weight, per 100 parts by weight of the total amount composed of the monocarboxylic acid ester or the monocarboxylic acid esters of diglycerol and/or of triglycerol and these substitute active compounds and/or extenders.

According to another advantageous embodiment of the present invention, one or more monocarboxylic acid esters of diglycerol and/or one or more monocarboxylic acid esters of triglycerol are employed in combination with other deodorizing substances or substances which inhibit the growth of bacteria or destroy bacteria.

According to yet another advantageous embodiment of the present invention, one or more monocarboxylic acid esters of diglycerol and/or one or more monocarboxylic acid esters of triglycerol are employed in combination with monocarboxylic acid esters of glycerol (that is to say of "monoglycerol"). These monocarboxylic acid esters of glycerol assume the role of extenders and/or substitute active compounds here and are preferably employed in a concentration of up to 50 parts by weight, preferably up to 35 parts by weight, per 100 parts by weight of the total amount composed of the monocarboxylic acid ester or the monocarboxylic acid esters of diglycerol and/or of triglycerol and these monocarboxylic acid esters of glycerol.

Such monocarboxylic acid esters of glycerol are favourably characterized by a structure as follows:

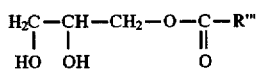

where R''' is a hydrocarbon radical, advantageously a branched or unbranched alkyl or alkenyl radical having 5 to 17 C atoms.

The deodorizing property of the esters according to the invention is primarily based on their selective activity against Gram-positive bacteria, in particular coryneform bacteria. These are regarded as the germs which are chiefly responsible for decomposition of apocrine perspiration.

The esters according to the invention furthermore have a good action against staphylococci.

Since the esters according to the invention at the same time are completely harmless to humans and other warm-blooded animals, they are ideally suitable for use in cosmetic deodorants.

The cosmetic deodorants according to the invention are particularly advantageously characterized in that the monocarboxylic acid ester or esters of di- and/or triglycerol is or are present in concentrations of 0.01–10.00% by weight, preferably 0.05–5.00% by weight, particularly preferably 0.1–3.00% by weight, in each case based on the total weight of the composition.

According to the invention, the α,Ω-alkanedicarboxylic acids are preferably chosen from the group consisting of the substances which are described by the generic formula

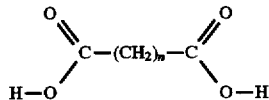

wherein n can assume numbers from 1 to 8.
n=1: malonic acid
n=2: succinic acid
n=3: glutaric acid
n=4: adipic acid
n=5: pimelic acid
n=6: suberic acid
n=7: azelaic acid
n=8: sebacic acid The use of I) one or more α,Ω-alkanedicarboxylic acids and II) one or more monocarboxylic acid esters of di- and/or triglycerol as the principle having the deodorizing action for cosmetic deodorants is thus advantageous according to the invention.

Cosmetic deodorants having a content of

I) adipic acid and/or azelaic acid and

II) one or more monocarboxylic acid esters of di- and/or triglycerol are regarded as a particularly advantageous embodiment of the present invention.

Cosmetic deodorants having a content of

I) one or more α,Ω-dicarboxylic acids and

II) diglycerol monocaprate are regarded as an especially advantageous embodiment of the present invention.

Cosmetic deodorants having a content of

I) adipic acid and/or azelaic acid and

II) diglycerol monocaprate are regarded as a preferred embodiment of the present invention.

The invention furthermore relates to a method of combating human body odour caused by microbial decomposition of apocrine perspiration, characterized in that an active amount of a mixture of I) one or more α,Ω-alkanedicarboxylic acids and II) one or more monocarboxylic acid esters of di- and/or triglycerol which can be present in a suitable cosmetic carrier, if appropriate, is applied to the skin.

Finally, the invention also relates to the use of a mixture of

I) one or more α,Ω-alkanedicarboxylic acids and

II) one or more monocarboxylic acid esters of di- and/or triglycerol for combating Gram-positive bacteria, in particular coryneform bacteria, and to the use of monocarboxylic acid esters of di- and/or triglycerol for preventing the growth of Gram-positive bacteria, in particular coryneform bacteria.

It is advantageous to choose the content of

I) one or more α,Ω-alkanedicarboxylic acids and

II) one or more monocarboxylic acid esters of di- and/or triglycerol such that ratios of I) and II) of 5:1 to 1:5, in particular about 1:1, are formed.

The cosmetic deodorants according to the invention are particularly advantageously characterized in that the monocarboxylic acid ester or esters of di- and/or triglycerol is or are present in concentrations of 0.05–10.00% by weight, preferably 0.1–5.0% by weight, in each case based on the total weight of the formulations.

The cosmetic deodorants according to the invention are particularly advantageously characterized in that the α,Ω-alkanedicarboxylic acid or the α,Ω-alkanedicarboxylic acids is or are present in concentrations of 0.01–10.00% by weight, preferably 0.05–5.0% by weight, in each case based on the total weight of the formulations.

The cosmetic deodorants according to the invention can be in the form of aerosols, that is to say preparations which can be sprayed from aerosol containers, squeeze bottles or by a pumping device, or in the form of liquid compositions which can be applied by means of roll-on devices, as deodorant sticks and in the form of W/O or O/W emulsions, for example creams or lotions, which can be applied from normal bottles and containers. The cosmetic deodorants furthermore can advantageously be in the form of deodorizing tinctures, deodorizing intimate cleansing agents, deodorizing shampoos, deodorizing shower or bath formulations, deodorizing powders or deodorizing powder sprays.

In addition to water, ethanol and isopropanol, glycerol and propylene glycol, customary cosmetic carriers for the preparation of the deodorizing formulations according to the invention which can be employed are skin-care fatty or fat-like substances, such as decyl oleate, cetyl alcohol, cetylstearyl alcohol and 2-octyldodecanol, in the ratios of amounts customary for such preparations, as well as swelling substances and thickeners, for example hydroxyethyl- or hydroxypropylcellulose, polyvinylpyrrolidone, and in addition also, in small amounts, cyclic silicone oils (polydimethylsiloxanes) as well as liquid polymethylphenylsiloxanes of low viscosity.

Suitable propellants for cosmetic deodorants, according to the invention, which can be sprayed from aerosol containers are the customary known highly volatile liquified propellants, for example hydrocarbons (propane, butane or isobutane), which can be employed by themselves or as a mixture with one another. Compressed air can also advantageously be used.

The expert of course knows that there are propellant gases which are non-toxic per se and which would be suitable in principle for the present invention, but which should nevertheless be omitted because of an unacceptable action on the environment or other concomitant circumstances, in particular chlorofluorohydrocarbons (CFCs).

Emulsifiers which can be used in the formulations in a small amount, for example 2 to 5% by weight, based on the total composition, and which have proved suitable for the preparation of the cosmetic deodorants according to the invention which are advantageously to be applied to the desired areas of skin as liquid formulations by means of a roll-on device are nonionic types, such as polyoxyethylene fatty alcohol ethers, for example cetylstearyl alcohol polyethylene glycol ether having 12 or 20 added-on ethylene oxide units per molecule, cetylstearyl alcohol and sorbitan esters and sorbitan ester-ethylene oxide compounds (for example sorbitan monostearate and polyoxyethylene sorbitan monostearate), and long-chain higher molecular weight waxy polyglycol ethers.

In addition to the constituents mentioned, perfume, dyestuffs, antioxidants (for example α-tocopherol and its derivatives or butylated hydroxytoluene (BHT=2,6-di-tert-butyl-4-methylphenol) in amounts of 0.01 to 0.03%, based on the total composition), suspending agents, buffer mixtures or other customary cosmetic bases, can be added to the deodorizing cosmetic formulations according to the invention, the pH of which is preferably adjusted, for example, to 4.0 to 7.0, in particular 5.0 to 6.5, by customary buffer mixtures.

The pH of the cosmetic deodorants according to the invention is preferably adjusted such that the acid components according to the invention are essentially present as acids and not as anions, that is to say preferably in the acid to neutral range, in particular in the pH range from 5.0 to 6.5.

The particular amounts of cosmetic carriers and perfume to be employed can easily be determined by the expert by simple trial and error according to the nature of the particular product.

Those substances and perfume oils which are stable, do not irritate the skin and already have antibacterial or bacteriostatic properties as such are also suitable, where appropriate, for perfuming.

Apart from special formulations which are in each case noted separately in the examples, the cosmetic formulations are prepared in the customary manner, usually by simple mixing, while stirring and if appropriate with gentle heating. The preparation presents no difficulties. For emulsions, the fatty phase and the aqueous phase are prepared separately, for example, if appropriate by heating, and then emulsified.

The usual rules for composing cosmetic formulations, with which the expert is familiar, otherwise apply.

If the compositions according to the invention are to be incorporated into powder sprays, the suspension bases for this can advantageously be chosen from the group consisting of silicic acid gels (for example those which are obtainable under the trade name Aerosil®), kieselguhr, talc, modified starch, titanium dioxide, silk powder, nylon powder, polyethylene powder and related substances.

Advantageous embodiment examples of the present invention follow. The numerical values stated are always in % by weight, based on the total composition, unless expressly noted otherwise.

| Examples 1–4 | | | | |
|---|---|---|---|---|
| Pump spray | 1 | 2 | 3 | 4 |
| Ethanol | 60.00 | 63.00 | 60.00 | 60.00 |
| Propylene glycol | 3.00 | 2.50 | 3.00 | 3.00 |
| PEG 40-hydrogenated castor oil | 2.50 | 2.50 | 2.50 | 2.00 |
| Adipic acid | 0.45 | 0.30 | — | — |
| Azelaic acid | — | — | 0.35 | 0.30 |
| α-Hydroxypalmitic acid | — | 0.25 | — | — |
| DMC | 0.30 | — | — | — |
| DML | — | 0.30 | — | — |
| TML | — | — | 0.30 | — |
| TMM | — | — | — | 0.30 |
| Perfume | q.s. | q.s. | q.s. | q.s. |
| Water, 10% strength NaOH to pH 5 | to 100.00 | | | |

| Examples 5–6 | | |
|---|---|---|
| Roll-on gel | 5 | 6 |
| Ethanol | 50.00 | 45.00 |
| Hydroxyethylcellulose | 0.50 | 0.50 |
| Steareth-20 ("Brij 78R") | 1.50 | 1.50 |
| Adipic acid | — | 0.50 |
| Azelaic acid | 0.45 | — |
| DMC | 0.30 | — |
| DML | — | 0.30 |
| Perfume | q.s. | q.s. |
| Water, 10% strength NaOH to pH 5 | to 100.00 | |

| Examples 7–8 | | |
|---|---|---|
| Roll-on emulsion (O/W) | 7 | 8 |
| Steareth-10 ("Brij 76R") | 4.00 | 4.00 |
| Cetyl alcohol | 2.00 | 1.50 |
| Mineral oil DAB 9 | 7.00 | 7.00 |
| PPG-15 stearyl ether | 4.50 | 4.50 |
| Methylparaben | 0.20 | 0.20 |
| Dipropylene glycol | 2.50 | 2.50 |
| Adipic acid | 0.80 | — |
| Succinic acid | — | 1.10 |
| DMC | 0.30 | — |
| DML | — | 0.30 |
| Perfume | q.s. | q.s. |
| Water, 10% strength NaOH to pH 5 | to 100.00 | |

| Examples 9–10 | | |
|---|---|---|
| Wax stick (anhydrous) | 9 | 10 |
| Trilaurin | 38.00 | 38.00 |
| Caprylic/capric triglyceride ("Miglyol 812R") | 29.50 | 29.50 |
| Glyceryl stearate, self-emulsifying | 8.50 | 8.50 |
| Beeswax | 21.00 | 21.00 |
| Adipic acid | 0.50 | — |
| Azelaic acid | — | 0.60 |
| DMC | 0.30 | — |
| DML | — | 0.30 |
| Perfume | q.s. | q.s. |
| Water, 10% strength NaOH to pH 5 | to 100.00 | |

We claim:

1. Cosmetic deodorants comprising mixtures of

I) one or more α,Ω-alkanedicarboxylic acids and

II) one or more monocarboxylic acid esters of di- and/or triglycerol.

2. Cosmetic deodorants according to claim 1, wherein the α,Ω-alkanedicarboxylic acid or acids are compounds of the formula

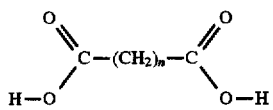

where n represents numbers from 1 to 8.

3. Cosmetic deodorants according to claim 1, wherein the α,Ω-dicarboxylic acids are adipic acid and/or azelaic acid.

4. Cosmetic deodorants according to claim 1, wherein the α,Ω-alkanedicarboxylic acids are present in concentrations of from 0.01–10.00% by weight, based on the total weight of the formulations.

5. Cosmetic deodorants according to claim 1, wherein the monocarboxylic acid ester or esters of diglycerol are compounds of the following structure:

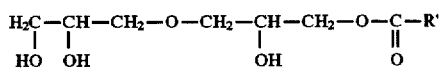

where $R^1$ is a hydrocarbon radical.

6. Cosmetic deodorants according to claim 1, wherein the monocarboxylic acid esters of triglycerol are compounds of the following structure:

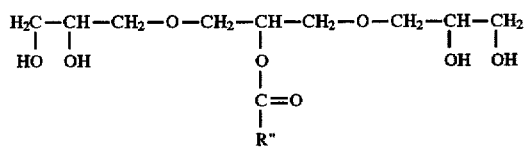

where $R^1$ is a hydrocarbon radical.

7. Cosmetic deodorants according to claim 1, wherein the monocarboxylic acid ester or esters of di- or triglycerol are selected from the group consisting of diglycerol monocaprate (DMC), triglycerol monolaurate (TML), diglycerol monolaurate (DML) and triglycerol monomyristate (TMM).

8. Cosmetic deodorants according to claim 1, wherein the content of

I) one or more α,Ω-alkanedicarboxylic acids and

II) one or more monocarboxylic acid esters of di- and/or triglycerol is chosen such that ratios of I) and II) of 5:1 to 1:5 are formed.

9. Cosmetic deodorants according to claim 1, wherein the monocarboxylic acid or esters of di- and/or triglycerol are present in concentrations of 0.05–10.00% by weight, based on the total weight of the formulations.

10. Cosmetic deodorants according to claim 4, wherein said α,Ω-alkanedicarboxylic acids are present in concentrations of from 0.05 to 5.0% by weight.

11. Cosmetic deodorants according to claim 4, wherein $R^1$ can be a branched or unbranched alkyl or alkenyl radical having 5 to 17 carbon atoms.

12. Cosmetic deodorants according to claim 6, wherein $R^{11}$ can be a branched or unbranched alkyl or alkenyl radical having 5 to 17 carbon atoms.

13. Cosmetic deodorants according to claim 6, wherein the ratio is about 1:1.

14. Cosmetic deodorants according to claim 9, wherein said ester or esters of di- and/or triglycerol are present in concentrations of 0.1 to 5% by weight.

* * * * *

UNITED STATES PATENT AND TRADEMARK OFFICE
CERTIFICATE OF CORRECTION

PATENT NO. : 5,718,887
DATED : February 17, 1998
INVENTOR(S) : Wolf, et al.

It is certified that error appears in the above-identified patent and that said Letters Patent is hereby corrected as shown below:

Col. 9, claim 5 last line    Delete " $R^1$ " and substitute -- $R'$ --

Col. 9, last line    Delete " $R^1$ " and substitute -- $R''$ --

Col. 10, line 21    Delete claim " 4 " and substitute -- 5 --, delete " $R^1$ " and substitute -- $R'$ --

Col. 10, line 25    Delete " $R^{11}$ " and substitute -- $R''$ --

Col. 10, line 29    Delete claim " 6 " and substitute -- 8 --

Signed and Sealed this

Twenty-fifth Day of May, 1999

Attest:

Q. TODD DICKINSON

Attesting Officer

Acting Commissioner of Patents and Trademarks